(12) United States Patent
Fedie

(10) Patent No.: US 7,137,991 B2
(45) Date of Patent: Nov. 21, 2006

(54) MULTI-WIRE EMBOLIC PROTECTION FILTERING DEVICE

(75) Inventor: Byron Fedie, Maple Grove, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 698 days.

(21) Appl. No.: 10/373,004

(22) Filed: Feb. 24, 2003

(65) Prior Publication Data

US 2004/0167564 A1    Aug. 26, 2004

(51) Int. Cl.
A61M 29/00 (2006.01)

(52) U.S. Cl. .................................................. 606/200
(58) Field of Classification Search ................ 606/200, 606/113, 114, 127, 159, 192–198, 108
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,494,531 A | 1/1985 | Gianturco | |
| 4,590,938 A | 5/1986 | Segura et al. | |
| 4,619,246 A | 10/1986 | Molgaard-Nielsen et al. | |
| 4,643,184 A | 2/1987 | Mobin-Uddin | |
| 4,650,466 A | 3/1987 | Luther | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A * | 1/1989 | Kletschka ................ | 606/194 |
| 4,807,626 A | 2/1989 | McGirr | |
| 4,873,978 A | 10/1989 | Ginsburg | |
| 4,921,478 A | 5/1990 | Solano et al. | |
| 4,921,484 A | 5/1990 | Hillstead | |
| 4,926,858 A | 5/1990 | Gifford, III et al. | |
| 4,969,891 A | 11/1990 | Gewertz | |
| 4,998,539 A | 3/1991 | Delsanti | |
| 5,002,560 A | 3/1991 | Machold et al. | |
| 5,011,488 A | 4/1991 | Ginsburg | |
| 5,053,008 A | 10/1991 | Bajaj | |
| 5,071,407 A | 12/1991 | Termin et al. | |
| 5,100,423 A | 3/1992 | Fearnot | |
| 5,102,415 A | 4/1992 | Guenther et al. | |
| 5,133,733 A | 7/1992 | Rasmussen et al. | |
| 5,152,771 A | 10/1992 | Sabbaghian et al. | |

(Continued)

FOREIGN PATENT DOCUMENTS

DE    28 21 048    7/1980

(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).

(Continued)

Primary Examiner—Kevin T. Truong
(74) Attorney, Agent, or Firm—Crompton, Seager & Tufte LLC

(57) ABSTRACT

An embolic protection filtering device and method of making and using the same. The present invention comprises a filtering device including an elongate shaft and a filter that may be releasably attachable to the shaft. The filter may include a coupling member that may be used to secure the filter to the shaft.

15 Claims, 9 Drawing Sheets

U.S. PATENT DOCUMENTS

| | | |
|---|---|---|
| 5,152,777 A | 10/1992 | Goldberg et al. |
| 5,160,342 A | 11/1992 | Reger et al. |
| 5,224,953 A | 7/1993 | Morgentaler |
| 5,324,304 A | 6/1994 | Rasmussen |
| 5,329,942 A | 7/1994 | Gunther et al. |
| 5,330,484 A | 7/1994 | Gunther |
| 5,354,310 A | 10/1994 | Garnie et al. |
| 5,370,657 A | 12/1994 | Irie |
| 5,376,100 A | 12/1994 | Lefebvre |
| 5,383,887 A | 1/1995 | Nadal |
| 5,421,832 A | 6/1995 | Lefebvre |
| 5,423,742 A | 6/1995 | Theron |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,725,550 A | 3/1998 | Nadal |
| 5,728,066 A | 3/1998 | Daneshvar |
| 5,746,767 A | 5/1998 | Smith |
| 5,749,848 A | 5/1998 | Jang et al. |
| 5,769,816 A | 6/1998 | Barbut et al. |
| 5,772,609 A | 6/1998 | Nguyen et al. |
| 5,779,716 A | 7/1998 | Cano et al. |
| 5,792,157 A | 8/1998 | Mische et al. |
| 5,795,322 A | 8/1998 | Bouewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,139,510 A | 10/2000 | Palermo |
| 6,142,987 A | 11/2000 | Tsugita |
| 6,152,144 A | 11/2000 | Lesh et al. |
| 6,152,946 A | 11/2000 | Broome et al. |
| 6,165,200 A | 12/2000 | Tsugita et al. |
| 6,168,579 B1 | 1/2001 | Tsugita |
| 6,168,604 B1 | 1/2001 | Cano |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,477 B1 | 8/2001 | Bagaoisan et al. |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,340,364 B1 * | 1/2002 | Kanesaka .................. 606/200 |
| 6,344,049 B1 | 2/2002 | Levinson et al. |
| 6,361,545 B1 | 3/2002 | Macoviak et al. |
| 6,361,546 B1 | 3/2002 | Khosravi |
| 6,371,971 B1 | 4/2002 | Tsugita et al. |
| 6,383,205 B1 | 5/2002 | Samson et al. |
| 6,398,756 B1 | 6/2002 | Peterson et al. |
| 6,423,032 B1 | 7/2002 | Parodi |
| 6,468,291 B1 | 10/2002 | Bates et al. |
| 6,485,501 B1 | 11/2002 | Green |
| 6,491,712 B1 * | 12/2002 | O'Connor .................. 606/200 |
| 6,506,203 B1 | 1/2003 | Boyle et al. |
| 6,511,503 B1 | 1/2003 | Burkett et al. |
| 2001/0044632 A1 | 11/2001 | Daniel et al. |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |

| | | |
|---|---|---|
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," AJR, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," Surgery, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," Cardiovascular Surgery, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," Catheterization and Cardiovascular Diagnosis, 31:17-84 (1994).

Moussa, MD, Issam "Stents Don't Require Systemic Anticoagulation . . . But the Technique (and Results) Must be Optimal," Journal of Invasive Cardiol., 8(E):3E-7E, (1996).

Nakanishi et al., "Catheter Intervention to Venous System Using Expandable Metallic Stents," Rinsho Kyobu Geka, 14(2):English Abstract Only (Apr. 1994).

Onal et al., "Primary Stenting for Complex Atherosclerotic Plaques in Aortic and Iliac Stenoses," Cardiovascular & Interventional Radiology, 21(5):386-392 (1998).

Theron et al., "New Triple Coaxial Catheter System for Carotid Angioplasty with Cerebral Protection," American Journal of Neuroradiology, 11:869-874 (1990).

Tunick et al., "Protruding atherosclerotic plaque in the aortic archo f patients with systemic embolization: A new finding seen by transesophageal echocardiography," American Heart Journal 120(3):658-660 (Sep. 1990).

Waksman et al., "Distal Embolization is Common After Directional Atherectomy . . . ," American Heart Journal, 129(3):430-435 (1995).

Wholey, Mark H. et al., PTA and Stents in the Treatment of Extracranial Circulation, *The Journal of Invasive Cardiology*, 8(E):25E-30E (1996).

\* cited by examiner

MULTI-WIRE EMBOLIC PROTECTION FILTERING DEVICE

FIELD OF THE INVENTION

The present invention pertains to filtering devices. More particularly, the present invention pertains to embolic protection filtering devices that are compatible with a number of different shafts.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

BRIEF SUMMARY

The invention provides design, material, manufacturing method, and use alternatives for intravascular filtering devices. In at least some embodiments, these filtering devices include an embolic protection filter that is adapted to be releasably attachable to a shaft. These and other desirable features are described in greater detail below.

DETAILED DESCRIPTION

Figure 1:
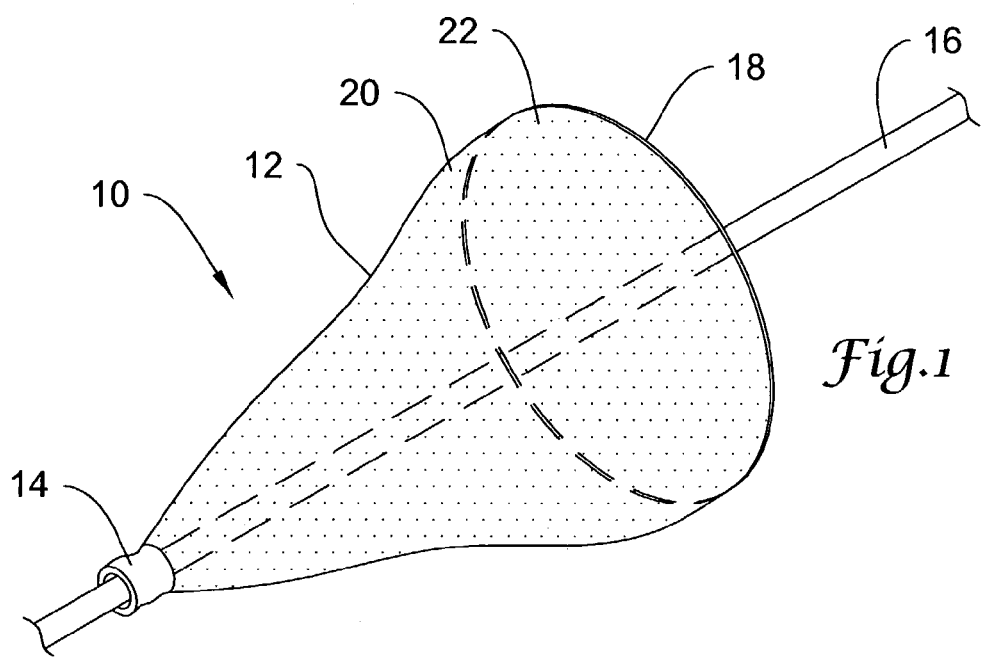
FIG. 1 is perspective view of an example filtering device.

The following description should be read with reference to the drawings wherein like reference numerals indicate like elements throughout the several views. The detailed description and drawings illustrate example embodiments of the claimed invention.

FIG. 1 is a side view of an example filtering device 10 including a filter 12 having a distal coupling member 14. Coupling member 14 may be adapted and configured for releasably attaching filter 12 to a shaft 16. This structural feature may provide filtering device 10 with a number of desirable features. For example, coupling member 14 may allow filter 12 to be attached to essentially any shaft such as virtually any of the various commercially available guidewires. This and other desirable features are described in more detail below.

In general, filter 12 may be adapted to operate between a first generally collapsed configuration and a second generally expanded configuration for collecting debris in a body lumen. In some embodiments, filter 12 can be delivered to an appropriate intravascular location, for example "downstream" of an intravascular lesion, using an appropriate filter delivery device. Similarly, filter 12 can be removed from the vasculature at the desired time by an appropriate filter retrieval device.

Filter 12 may include a filter frame 18 and a filter membrane or fabric 20 coupled to filter frame 18. Frame 18 may take the form of any one of a number of appropriate shapes and configurations. For example, frame 18 may comprise a generally circular filter mouth or loop, which may defines the primary opening for blood to travel into and be filtered by filter 12. However, essentially any appropriate shape or configuration may be utilized without departing from the spirit of the invention.

Frame 18 may be comprised of any appropriate material. For example, frame 18 may be comprised of a "self-expanding" shape-memory material such as nickel-titanium alloy (to bias filter 12 to be in the second expanded configuration). Alternatively, frame 18 may be comprised of essentially any appropriate metal, metal-alloy, polymer, combinations thereof, and the like including any of the materials described herein. In some embodiments, frame 18 or portions thereof may be doped with, plated with, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, plastic material loaded with a radiopaque filler, and the like. For example, a radiopaque wire disposed about a portion of frame 18.

Filter membrane 20 may be comprised of any appropriate material such as a polymer and may be drilled (for example, formed by known laser techniques) or otherwise include at least one opening 22. Holes or openings 22 can be sized to allow blood flow therethrough but restrict flow of debris or emboli floating in the body lumen or cavity.

The embodiment shown in FIG. 1 illustrates shaft 16 as being a guidewire. However, shaft 16 is not intended to be limited to being only a guidewire. It can be appreciated that shaft 16 may comprise number of different structures including a catheter (e.g., therapeutic, diagnostic, or guide catheter), endoscopic device, laproscopic device, an embolic protection device, or any other suitable device. In some embodiments, shaft 16 may comprise a tubular filter cartridge. According to this embodiment, filtering device 10 can be configured to be slidable over a guidewire or other suitable medical device.

Coupling member 14 may comprise a number of different materials including polymers. Some examples of suitable polymers may include polytetrafluoroethylene (PTFE), fluorinated ethylene propylene (FEP), polyurethane, polypropylene (PP), polyvinylchloride (PVC), polyether-ester (for example a polyether-ester elastomer such as ARNITEL® available from DSM Engineering Plastics), polyester (for example a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene, Marlex high-density polyethylene, linear low density polyethylene (for example REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), electroactive polymers (i.e., polymers that respond to electrical stimulation), ferromagnetic polymers (i.e., polymers that respond to energy such as radiofrequency energy), other suitable materials, or mixtures, combinations, or copolymers thereof. In some embodiments coupling member 14 can include a liquid crystal polymer (LCP) blended with other polymers to enhance torqueability. Coupling member 14 may also be doped with or otherwise include radiopaque materials including those described herein.

In some embodiments, coupling member 14 may be comprised other materials such as metals, metal alloys, metal-polymer composites, and the like. For example, coupling member 14 may comprise a shape memory allow such as nickel-titanium alloy such as nitinol, nickel-chromium alloy, nickel-chromium-iron alloy, and the like. These may allow for coupling member 14, for example, to more securely attach to shaft 16.

In some embodiments, a coating, for example a lubricious, a hydrophilic, a protective, or other type of coating may be applied over portions or all of coupling member 14, or other portions of device 10. Hydrophobic coatings such as fluoropolymers provide a dry lubricity which improves device handling and exchanges. Lubricious coatings improve steerability and improve lesion crossing capability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

Coupling member 14 may comprise a number of different shapes. For example, coupling member 14 may be generally cylindrical in shape as shown in FIG. 1. Alternatively, coupling member 14 may comprise other shapes including those similar to an o-ring, tire, donut, oval, and the like. It can be appreciated that coupling member 14 may be essentially any appropriate shape. Additionally, the size and/or length of coupling member 14 may vary. For example, coupling member may be about 1 mm to about 2 mm in length or longer.

In at least some embodiments, coupling member 14 may comprise an elastic material that would frictionally attach filter 12 to shaft 16. Accordingly, a user can exert sufficient force to slide filter 12 over shaft 16. Upon sliding filter 12 to the desired location along shaft 16, the position of the filter 12 can then be substantially maintained by the frictional fit between filter 12 and shaft 16. Alternatively, coupling member 14 may comprise a swellable material that swells when exposed to an appropriate stimuli. In still other embodiments, coupling member 14 may include one or more chemicals that, when combined or exposed to the appropriate stimui, react to cause expansion of coupling member 14 or otherwise change the configuration thereof so as to secure coupling member 14 to shaft 16.

Coupling member 14, or any of the other structural elements described herein, may include a drug or other substance that may elute or diffuse therefrom. For example, coupling member 14 may include an anti-coagulation drug such as heparin that may help discourage coagulation of blood adjacent coupling member 14. Other diagnostic and therapeutic substances may be included without departing from the spirit of the invention.

Figure 2:
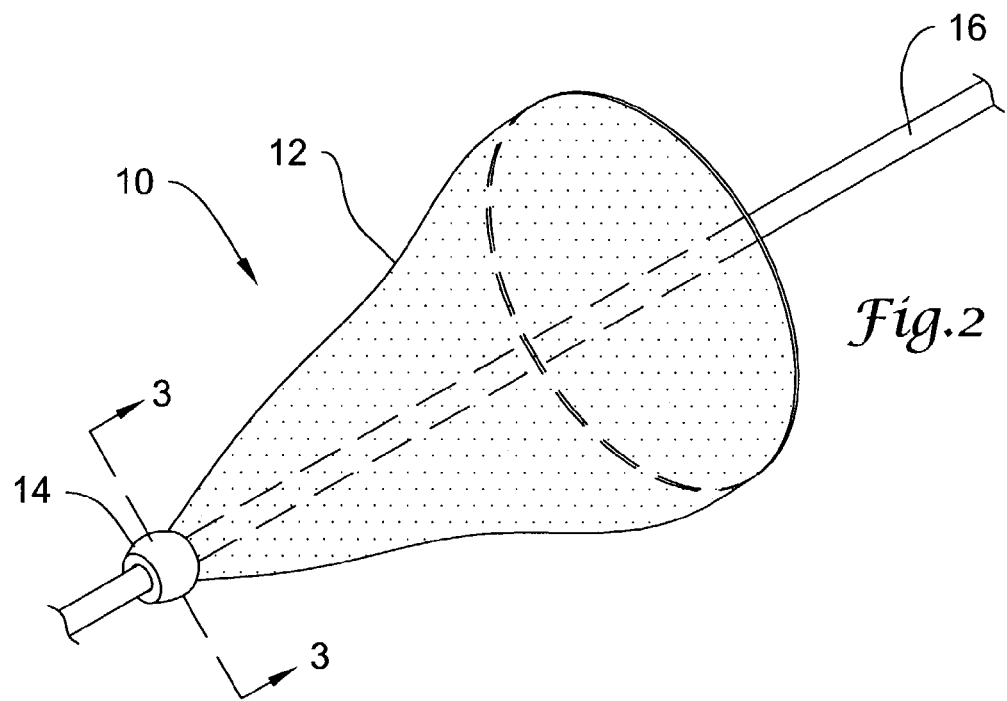
FIG. 2 is a perspective view of an example filtering device with an inflated coupling member.

In addition or as an alterative to the above embodiments, coupling member 14 may be inflatable. According to this embodiment, coupling member 14 can shift between at least a first and second configuration. The first configuration may be a generally deflated configuration, wherein filter 12 is slidable along shaft 16. The second configuration may be a generally inflated configuration, wherein the position of filter 12 is substantially fixed relative to shaft 16 as shown in FIG. 2. In use, for example, a user may advance filter 12 along shaft 16 to the desired position and then inflate coupling member 16 to secure filter 12 to shaft 16.

Figure 3:
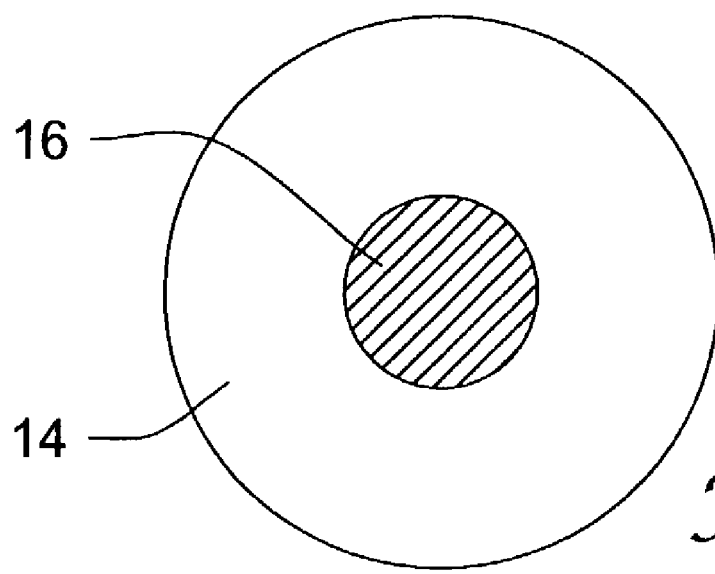
FIG. 3 is a cross-section view taken through line 3—3.
Figure 3A:
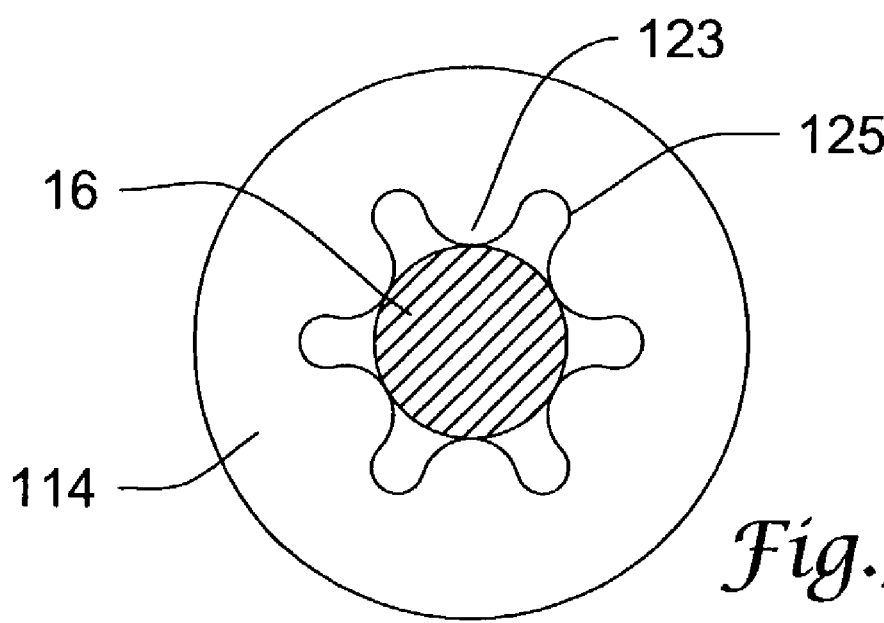
FIG. 3A is an alternative cross-section view taken through line 3—3.

FIG. 3 illustrates that, when inflated, coupling member 14 may exert a force on shaft 16 to secure filter 12 thereto. According to this embodiment, the inside surface of coupling member 14 may generally conform to the shape of shaft 16. Some alternative coupling members 114 may include one or more teeth 123 and/or dimples 125 on its inside surface as shown in FIG. 3A that may help strengthen the bond between coupling member 114 and shaft 16. According to this embodiment, when coupling member 114 is inflated, teeth 123 may facilitate the gripping force exerted by coupling member 114 on shaft 16. Teeth 123 and dimples 125 can vary in number, shape, arrangement, longitudinal length, etc.

Figure 4:
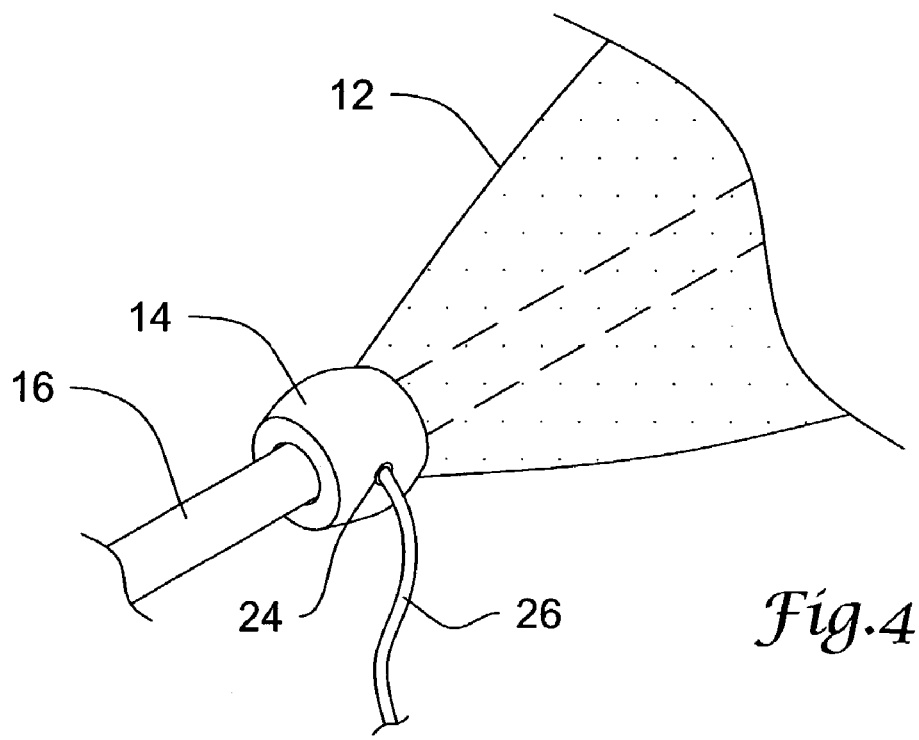
FIG. 4 is a perspective view of an example filtering device with an inflation tube attached to a coupling member.

Coupling member 14 may be inflated in a number of different ways. For example, FIG. 4 illustrates that coupling member 14 may include an inflation port 24 that is adapted to receive an inflation tube or member 26. Inflation of coupling member 14, thus, may include releasably coupling inflation tube 26 to inflation port 24, infusing inflation media into coupling member 14 to inflate it, and then removing inflation tube 26 from port 24. According to this embodiment, port 24 may include a valve or other suitable means to hermetically seal coupling member 14.

A number of alternative arrangements and/or devices may be utilized to inflate coupling member 14. For example, other medical devices such as catheters or guidewires that have inflation lumens may be disposed adjacent coupling member 14 and used to inflate it. According to this embodiment, a medical device can be advanced along shaft 16 to a position adjacent coupling member 14, configured so that the inflation lumen of the medical device is in fluid communication with coupling member 14, and then inflation media can be passed from the inflation lumen into coupling member 14.

Figure 5:
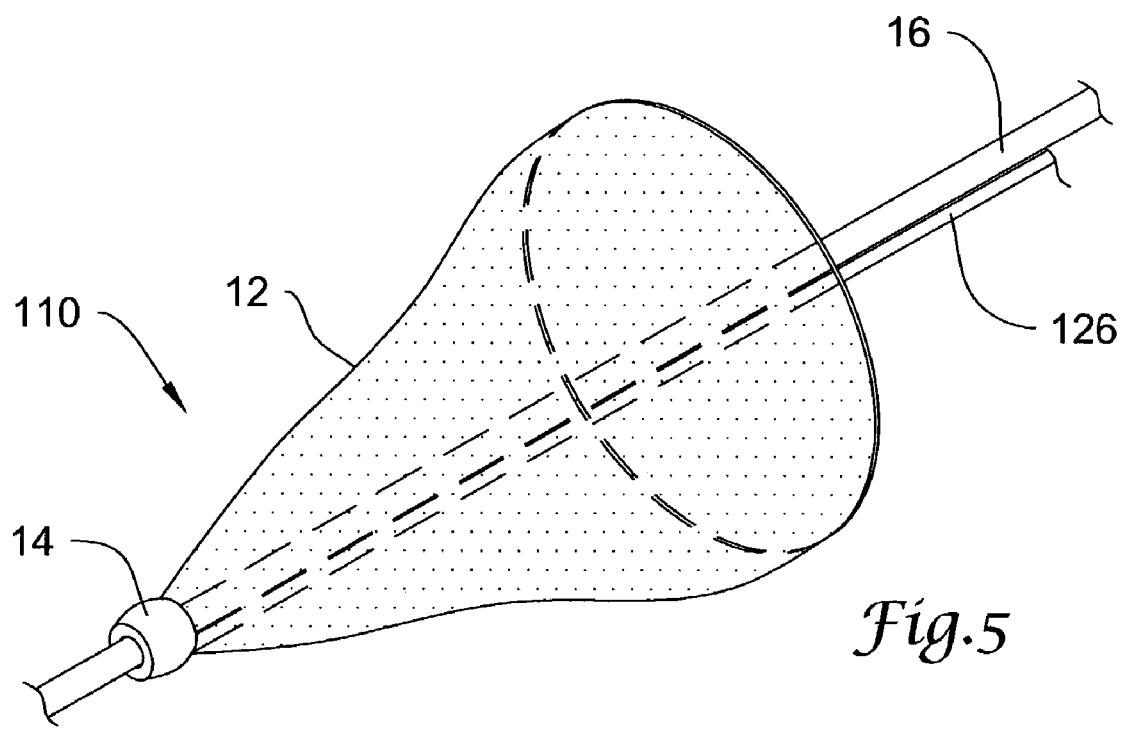
FIG. 5 is a perspective view of another example filtering device including an inflation tube.

An alternative filtering device 110 is depicted in FIG. 5. Device 110 is essentially the same in form and function as device 10, except that inflation tube 126 is adapted for being attached to coupling member 14 and extending proximally therefrom, for example adjacent or along shaft 16. This arrangement may allow filter 12 to be slid along a medical device already placed in a blood vessel. Once properly positioned, coupling member 14 can then be inflated to secure filter 12 to shaft.

Figure 6:
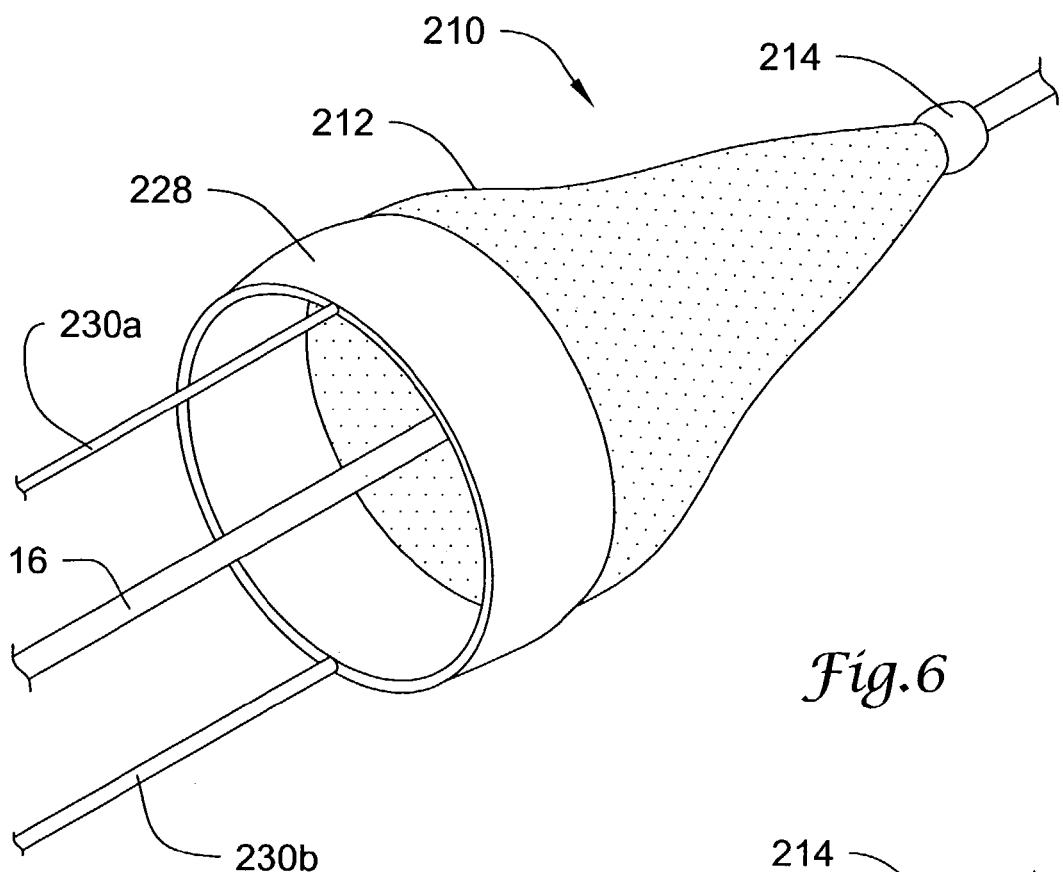
FIG. 6 is a perspective view of another example filtering device.

Another example filtering device 210 is shown in FIG. 6. Device 210 is essentially the same in form and function as any of the devices described herein except that filter 212 includes an expansion member 228. In at least some embodiments, expansion member 228 may comprise an inflatable cylinder that may, for example, be inflated to open or expand filter 212. According to this embodiment, one or more inflation tubes 230a/b may be coupled to expansion member 228 and extend proximally therefrom. Inflation tubes 230a/b may be attached to a suitable inflation device so that inflation medium may be infused through tubes 230a/b into expansion member 228 to inflate it and expand filter 212.

Expansion member 228 may also provide filtering device 210 (and/or filter 212) with a number of additional desirable features. For example, expansion member 228 may improve vessel wall apposition. This is because at least some embodiments of expansion member 228 are sufficiently compliant to conform to even the most irregularly shaped vessel wall. Thus, expansion member 228 may allow filter 212 to substantially seal essentially the entire circumference of the vessel wall.

Additionally, expansion member 228 may have a length that allows it to help secure filter 212 more securely within a blood vessel. This structural feature may allow filter 212 to maintain it position within the blood vessel even when subjected to potentially displacing forces associated with moving blood and/or debris. In some embodiments, the length may be on the order of, for example, about 4 mm to about 5 mm or more.

The materials, shape, and other features of expansion member 228 may be essentially the same as what is described above. For example, expansion member 228 may comprise a polymer that is generally cylindrical in shape. However, the shapes, materials, etc. can vary to include any appropriate configuration. In at least some embodiments, expansion member 228 (like any of the structural elements disclosed herein) may include a radiopaque material. The radiopaque materials may be dispersed throughout expansion member 228 or may be arranged in a specific, known banding pattern. This later feature, combined with a desirable length, may allow expansion member 228 to be used for both visualization of filter 212 and for measurement within a blood vessel.

In use, filtering device 210 may be placed within a blood vessel at an appropriate target region. The steps involved in placing and/or delivering device 210 may include a number of steps. For example, filter 212 may be advanced along shaft 16 to the desired location and secured thereto in an appropriate manner, for example by inflating coupling member 214. Advancing filter 212 may occur outside the body (where inflation of coupling member 214 may include releasably attaching an inflation tube as described in relation to FIG. 4 above) or within the body (where inflation of coupling member 214 may include passing inflation media through an inflation tube in a manner similar to what is described in relation to FIG. 5).

Figure 7:
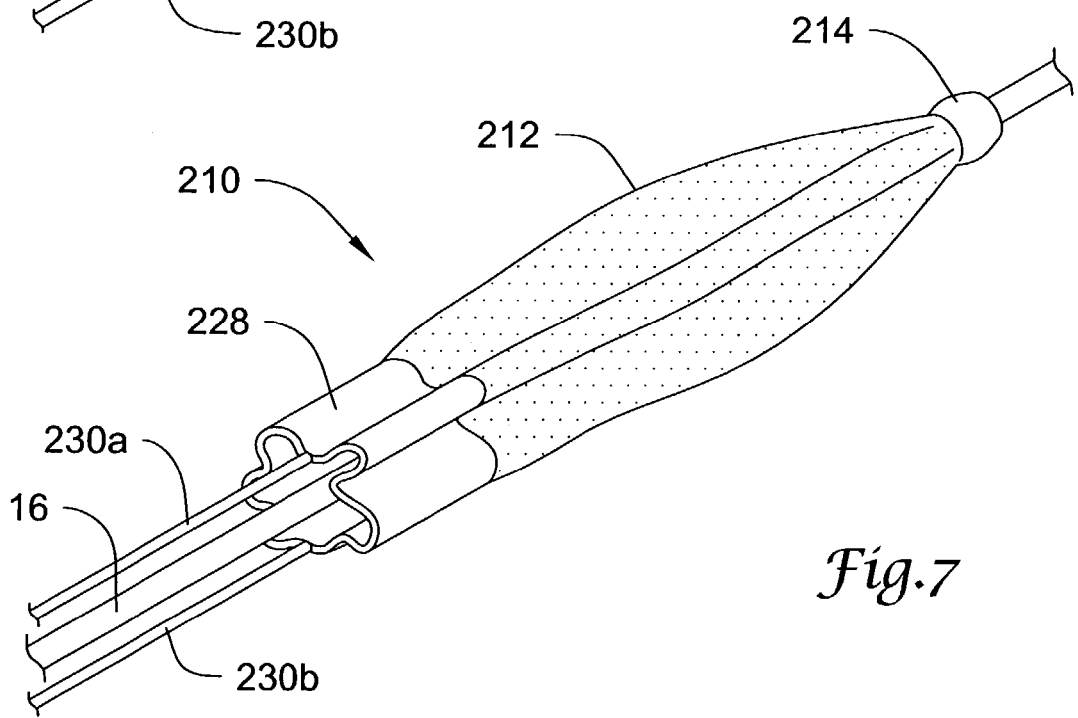
FIG. 7 is a perspective view of an example filtering device in a collapsed configuration.

Filter 212 (in a collapsed configuration as shown in FIG. 7) can be advanced through the blood vessel in a suitable manner such as with the use of an appropriate filter delivery device. Once properly positioned, expansion member 228 can be inflated to expand and open filter 212. Filter 212 can then be used to capture embolic debris.

Figure 8:
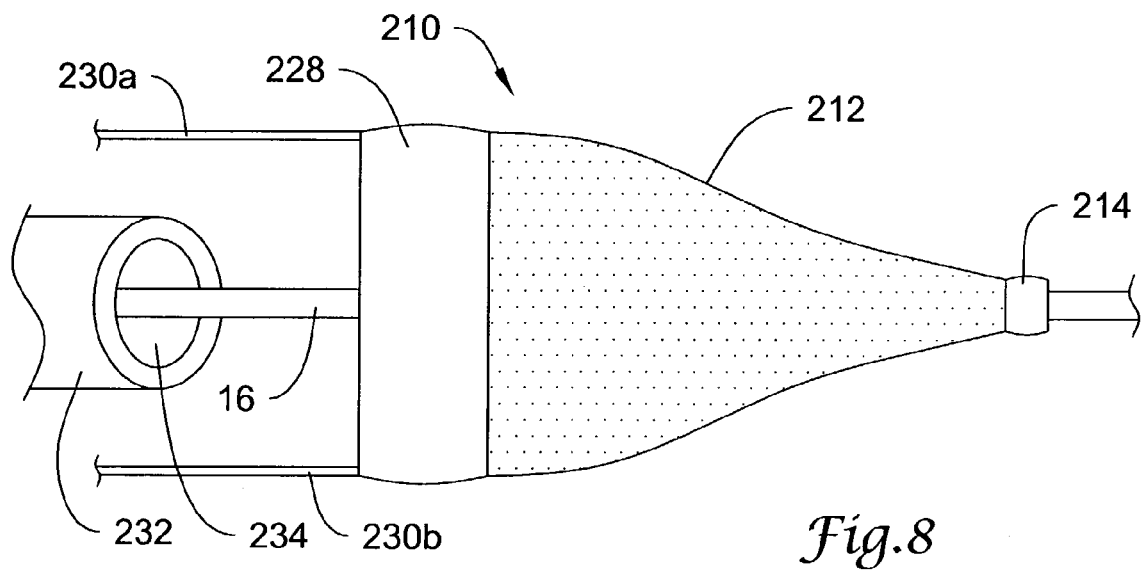
FIG. 8 is a side view of an example arrangement for a filtering device.

A diagnostic or treatment device 232 such as an angioplasty or atherectomy catheter can be advanced over shaft 16 to a position adjacent an intravascular lesion and "upstream" of filter 212 as shown in FIG. 8. Debris generated by the use of treatment device 232 can be captured by filter 212. Prior to or during the use of treatment device 232, expansion member 228 may be deflated. Even when deflated, it is believed that filter 212 will maintain its expanded or open configuration due to flow of blood through filter 212.

The arrangement of inflation tubes 230a/b in relation to treatment device 232 may vary. For example, inflation tubes 230a/b may be positioned so that tubes 230a/b run substantially parallel to the vessel wall as shown in FIG. 8. This arrangement may be desirable, for example, by allowing treatment device 232 to have a smaller profile by not requiring a lumen 234 that is large enough to accommodate tubes 230a/b. According to this embodiment, treatment device 232 may be advanced over shaft 16 and under tubes 230a/b.

Figure 9:
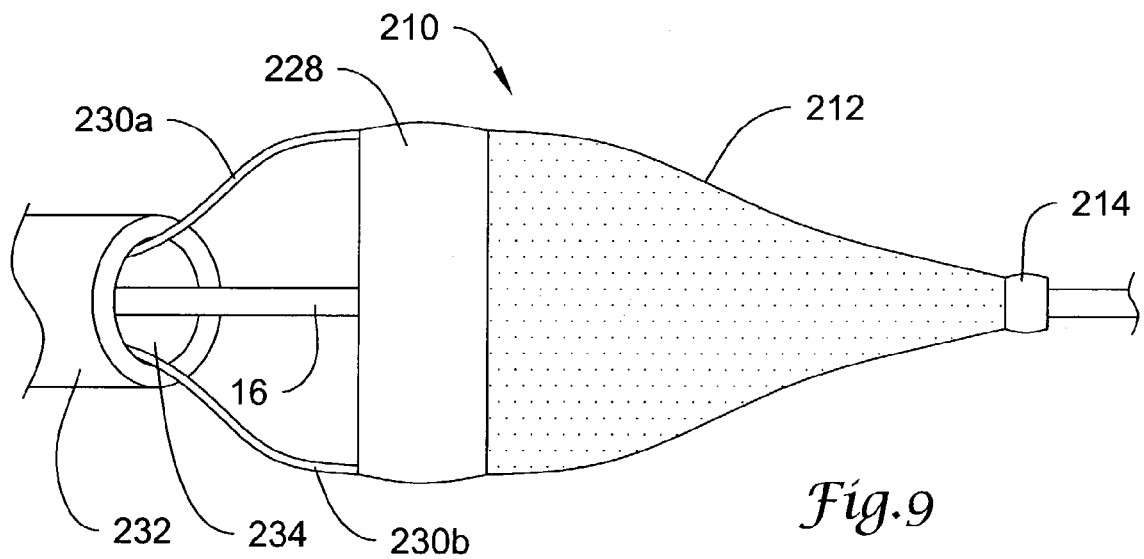
FIG. 9 is a side view of another example arrangement for a filtering device.

Alternatively, tubes 230a/b may be arranged to pass through lumen 234 of treatment device 232 as shown in FIG. 9. This arrangement may be desirable for a number of reasons. For example, if the intervention includes the placement of or the use of a stent, it may be desirable to keep tubes 230a/b from contacting and possibly displacing the stent. Additionally, passing tubes 230a/b through lumen 234 or through an analogous lumen of a suitable retrieval device may also aid in retrieval of filter 212. For example, as the retrieval device is advanced over shaft 16 and tubes 230a/b toward filter 212, tubes 230a/b may begin to exert an inward force on filter 212 (adjacent expansion member 228), which can aid in placing filter 212 within the retrieval device so that filter 212 can be removed from the vasculature.

Figure 10:
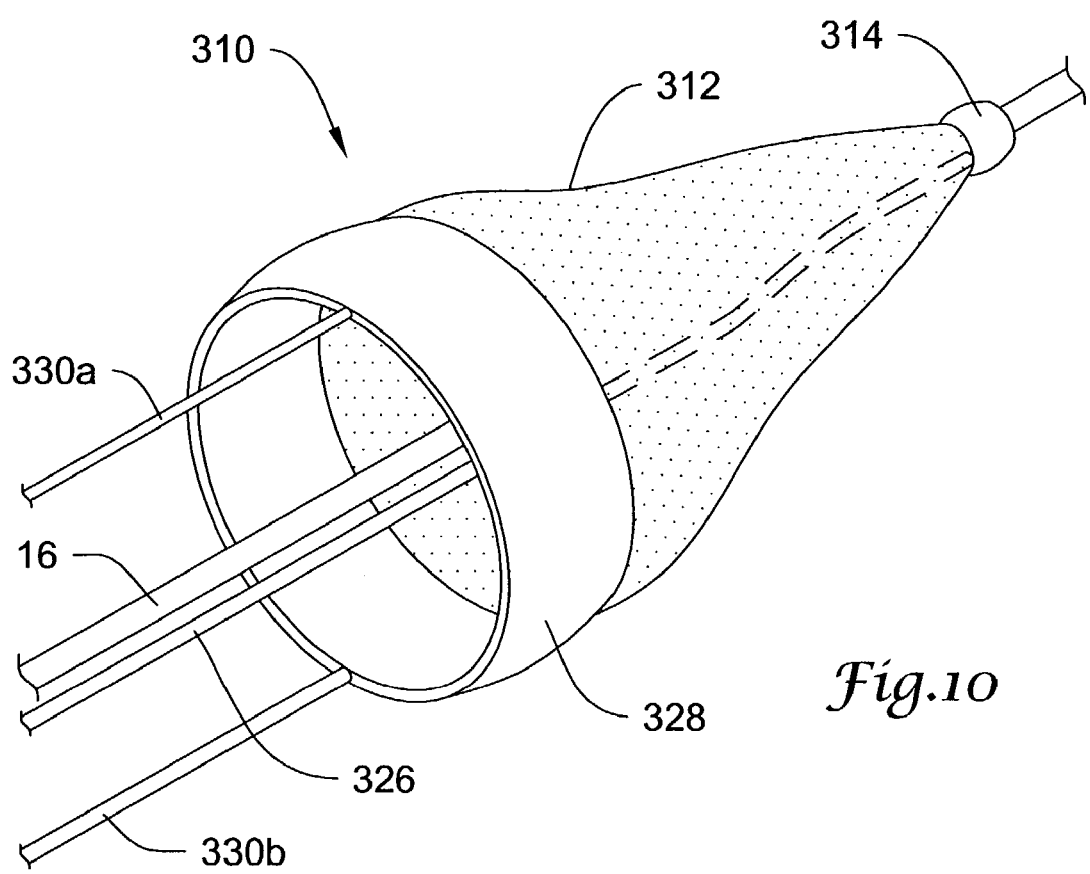
FIG. 10 is a perspective view of another example filtering device.

Another example filtering device 310 is shown in FIG. 10. Device 310 is similar to other devices described herein and includes filter 312 having coupling member 314, inflation tube 326 coupled to coupling member 314, expansion member 328, and inflation tubes 330a/b coupled to expansion member 328. This figure shows an example embodiment that essentially combines the structural features illustrated in FIGS. 5 and 6, and that may be used in a manner that is analogous to what is described in relation to FIGS. 5–9.

Figure 11:
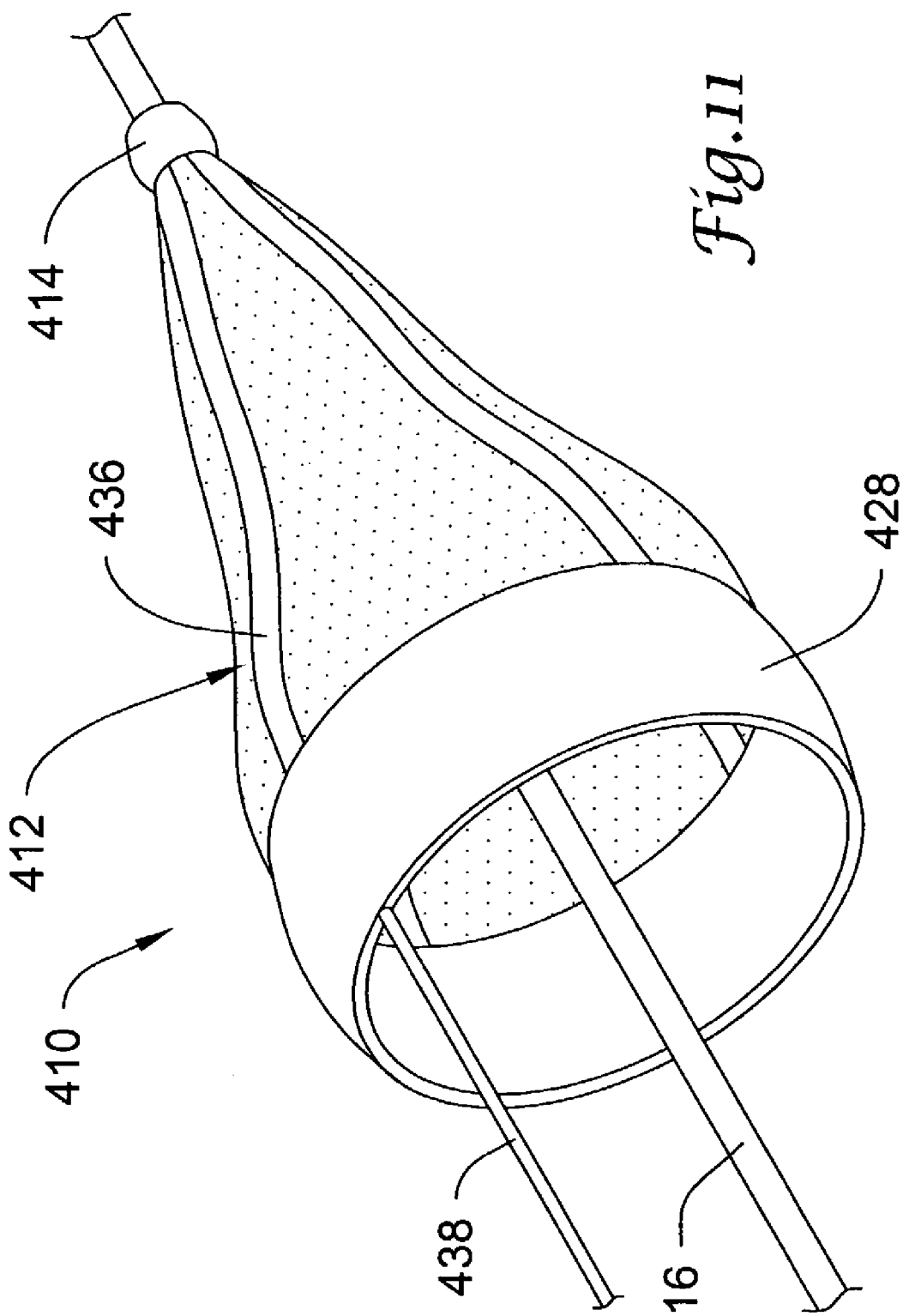
FIG. 11 is a perspective view of another example filtering device.

FIG. 11 is a cross-sectional view of another example filtering device 410. Device 410 is similar to other devices described herein and includes filter 412 having one or more longitudinal ribs 436 that may be disposed between expansion member 428 and coupling member 414. The precise location of ribs 436, however, may vary. Moreover, ribs 436 may be included with or without expansion member 428 and/or coupling member 414.

Ribs 436 may be inflatable so that upon inflation they can expand filter 412. Inflation of ribs 436 may occur in any one of a number of different ways. For example, an inflation tube 438 may be coupled to ribs 436 so that inflation media can be infused into ribs 436. In some embodiments, inflation tube 438 may be used to inflate any combination of the inflatable structural elements that are present (e.g., coupling member 414, expansion member 428, and ribs 436). Alternatively, any of the inflatable structures may include inflation tubes or other inflation means such as any of those described herein.

Figure 12:
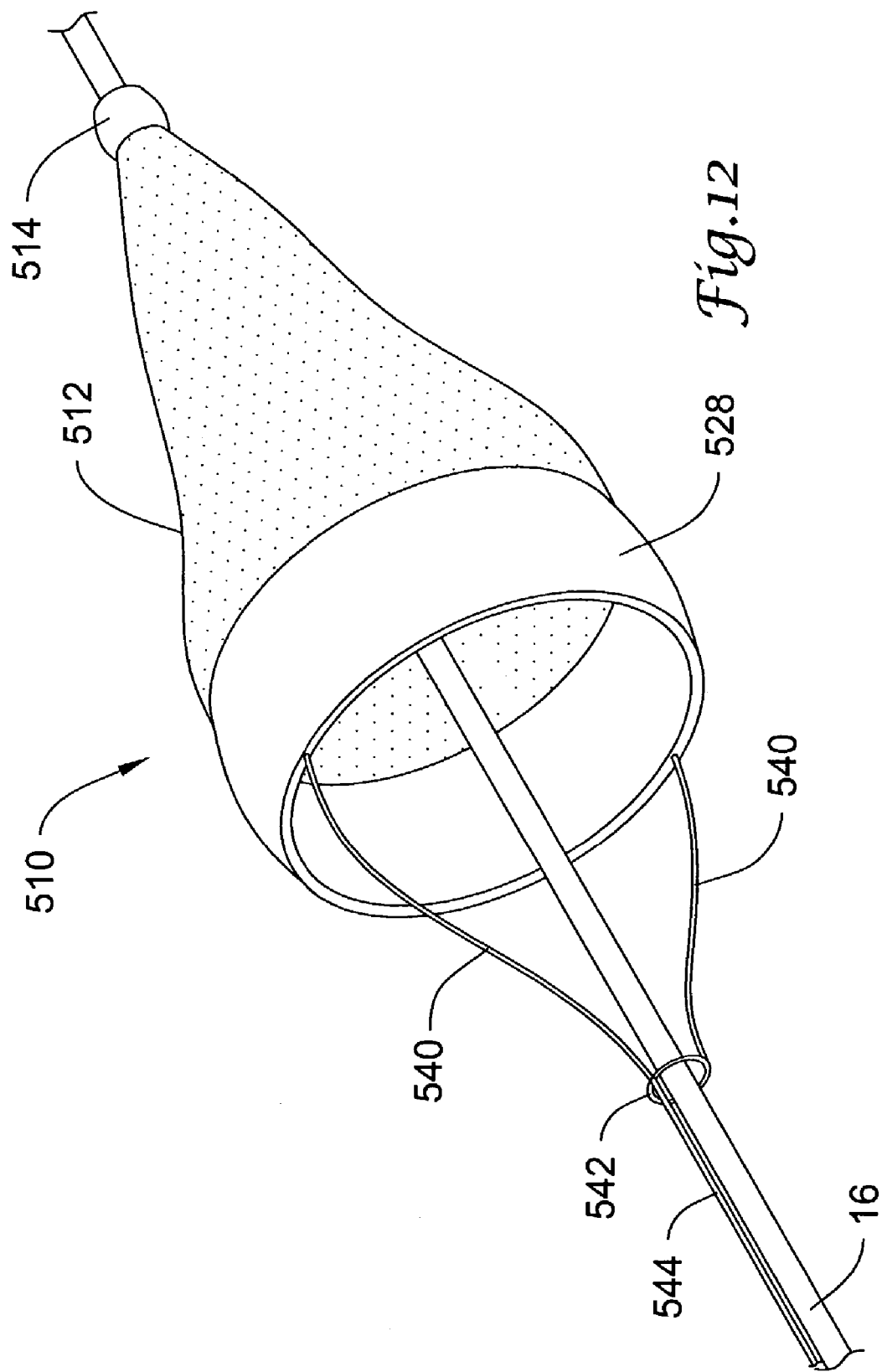
FIG. 12 is a perspective view of another example filtering device.

FIG. 12 is a perspective view of another example filtering device 510. Device 510 is essentially the same in form and function as any of the devices described herein, except that filter 512 may include one or more strut fibers 540 extending between filter 512 and a slip ring 542 disposed about shaft 16. A proximal fiber 544 may be coupled to slip ring 542 and extend proximally therefrom. According to this embodiment, proximally pulling on fiber 544 may shift slip ring 542 proximally and, consequently, at least partially collapse or close filter 512.

FIG. 12 also depicts device 510 as including expansion member 528 and coupling member 514. Inflation tubes or other inflation means for these structures may include any of those described herein and, for simplicity, are not included in FIG. 11. It can be appreciated that strut fibers 540, slip ring 542, and proximal fiber 554 may be included in any of the embodiments of filtering devices described herein.

Figure 13:
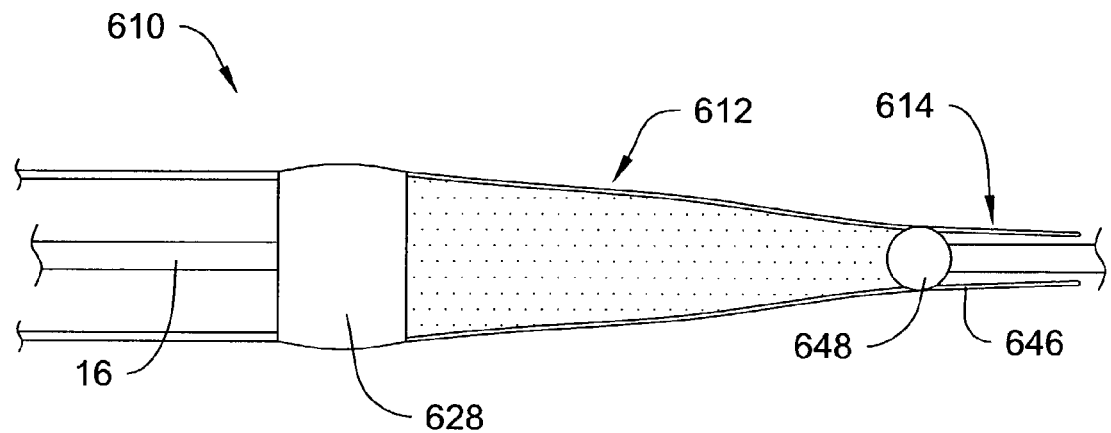
FIG. 13 is a perspective view of another example filtering device.
Figure 14:
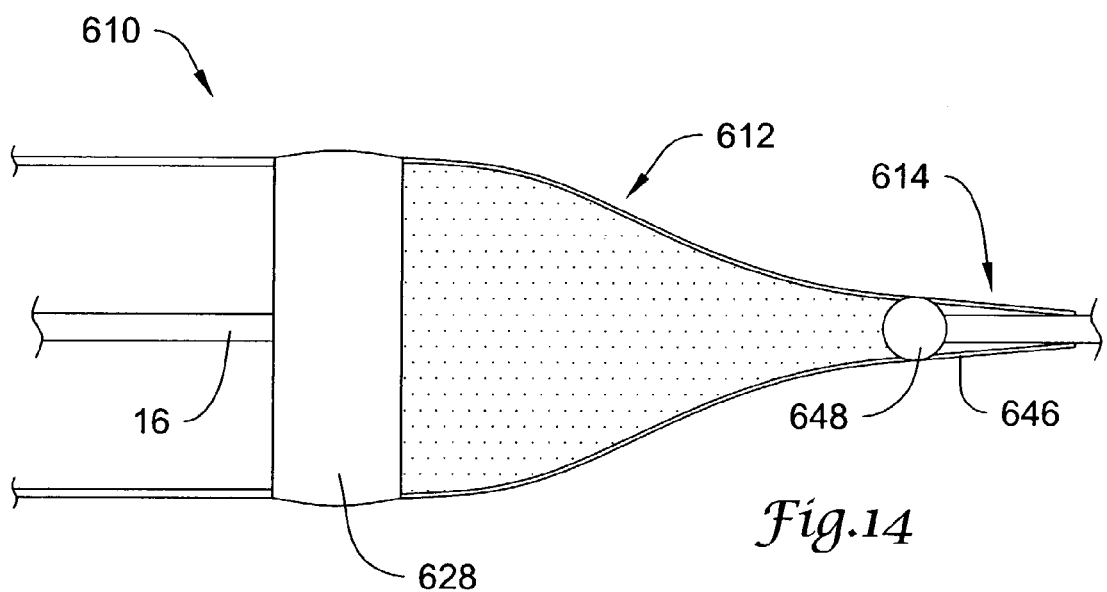
FIG. 14 is a perspective view of the filtering device of FIG. 13 where the expansion member is inflated.

FIG. 13 shows another example filtering device 610 that is similar to other devices described herein. Device 610 may include an alternative example coupling member 614 that includes one or more gripping arms 646 that can pivot about a pivot point 648 so as to secure filter 612 to shaft 16. According to this embodiment, as expansion member 628 is inflated and expands, arms 646 pivot about pivot point 648 and secure filter 612 to shaft 16 as shown in FIG. 14.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An embolic protection filtering device for coupling to an elongate shaft, comprising:
    a filter capable of being coupled to the elongate shaft, the filter including an inflatable coupling member and an inflatable expansion member; and
    wherein the inflatable coupling member is adapted to shift between a first deflated configuration in which the filter is slidable along the longitudinal axis of the shaft, and a second inflated configuration in which the position of the filter is substantially fixed relative to the shaft.

2. The filtering device of claim 1, wherein coupling member includes an inner surface and may include one or more teeth disposed along the inner surface.

3. The filtering device of claim 1, wherein the coupling member includes inflation port.

4. The filtering device of claim 3, further comprising an inflation tube coupled to the coupling member adjacent the inflation port.

5. The filtering device of claim 1, wherein the expansion member includes one or more inflation tubes.

6. The filtering device of claim 1, wherein the filter includes one or more inflatable longitudinal ribs.

7. The filtering device of claim 1, further comprising a slip ring disposed around the elongate shaft, one or more strut fibers extending between the filter and the slip member, and a proximal fiber attached to the slip ring and extending proximally therefrom.

8. An embolic protection filtering device, comprising:
    an elongate shaft having a proximal end and a distal end;
    a filter coupled to the shaft, the filter including a proximal mouth region, a filter membrane region, a distal region, and an inflatable coupling member disposed at the distal region, a proximal expansion member coupled to the proximal mouth region; and
    wherein the inflatable coupling member is adapted to shift between a first deflated configuration in which the filter is slidable over the shaft, and a second inflated configuration in which the position of the filter is substantially fixed relative to the shaft.

9. The filtering device of claim 8, wherein the shaft comprises a guidewire.

10. The filtering device of claim 8, wherein inflatable coupling member includes an inflation port.

11. The filtering device of claim 10, further comprising an inflation tube detachably coupled to the inflation port.

12. The filtering device of claim 8, wherein the inflatable coupling member includes an inflation tube coupled thereto and extending proximally therefrom.

13. The filtering device of claim 8, wherein the proximal filter expansion member includes one or more inflation tubes coupled thereto and extending proximally therefrom.

14. The filtering device of claim 8, further comprising one or more inflatable longitudinal ribs.

15. The filtering device of claim 8, further comprising a slip ring disposed on the shaft and including a first wire attached to the filter and a second wire extending toward the proximal end of the shaft.

* * * * *